United States Patent [19]

Conrad et al.

[11] Patent Number: 5,707,617
[45] Date of Patent: Jan. 13, 1998

[54] BOVINE NEOSPORA ISOLATES

[75] Inventors: Patricia A. Conrad; Bradd C. Barr; Mark L. Anderson, all of Davis; Karen W. Sverlow, Vacaville, all of Calif.

[73] Assignee: The Regents of the University of California, Oakland, Calif.

[21] Appl. No.: 327,516

[22] Filed: Oct. 20, 1994

Related U.S. Application Data

[63] Continuation-in-part of Ser. No. 215,858, Mar. 21, 1994, abandoned.

[51] Int. Cl.$^6$ .................................................. C12N 1/10
[52] U.S. Cl. ........................................ 424/93.1; 435/258.1
[58] Field of Search ......................... 424/93.1; 435/258.1

[56] References Cited

PUBLICATIONS

Shivaprasad et al., Veterinary Parasitology 34 :145–148 (1989).
Anderson et al. JAVMA 198(2):241–2 44 (1991).
Dubey et al., Journal of Parsitology 76(5):732–734 (1990).
Dubey et al., JAVMA 201(5):709–713 (1992).
Barr, B.C., et al. (1990) "Bovine Fetal Encephalitis and Myocarditis Associated With Protozoal Infections", *Vet Pathol*, 27:354–361.
Barr, Brad C., et al. (1991) "Neospora–like encephalomyelitis in a calf: pathology, ultrastructure, and immunoreactivity"*J. Vet. Diagn. Invest*, 3:39–46.
Dubey, J.P., et al. (1988) "Neonatal *Neospora caninum* infection in dogs: Isolation of the causative agent and experimental transmission", *JAVMA*, 193(10):1259–1263.
Anderson, Mark L., et al. (1991) "Neospora–like protozoan infection as a major cause of abortion in California dairy cattle", *JAVMA*, 198(2) :241–244.
Dubey, J.P. (1992) "A Review of *Neospora caninum* and Neospora–like Infections in Animals", *J. Protozool. Res.*, 2:40–52.
Lindsay, David S., et al. (1993) "Neospora–Induced Protozoal Abortions in Cattle", *The Compendium*, 15(6) :882–889.
Conrad, Patricia A., et al. (1993) "Detection of serum antibody responses in cattle with natural or experimental Neospora infections", *J. Vet Diagn Invest*, 5:572–578.
Barr, B.C., et al. (1991) "Neospora–like Protozoal Infections Associated with Bovine Abortions", *Vet Pathol*, 28:110–116.
Conrad, P.A., et al. (1991) "In vitro isolation and characterization of a *Neospora* sp. from aborted bovine foetuses", *Parasitology*, 106:239–249.

*Primary Examiner*—Jean C. Witz
*Attorney, Agent, or Firm*—Townsend and Townsend and Crew LLP

[57] ABSTRACT

The present invention provides isolated bovine Neospora cultures. The cultures are used to develop diagnostic assays for the detection of Neospora infections in cattle and other animals. Also provided are pharmaceutical compositions for the treatment and prevention of Neospora infections.

2 Claims, 5 Drawing Sheets

$^1$INACURATION OF LACHYZOTTE (413, 416) OR UNINFECTED (408) CULTURES.
$^2$FETUSES RECOVERED BY CAESERIAN SECTION (413) OR AT EUTHANASIA (408)

$^1$CRITERIA FOR DETERMINING INFECTION STATUS IS AS DESCRIBED IN MATERIALS AND METHODS.
$^2$SERA COLLECTED FROM DAM AT TIME OF ABORTION OR CALVING.

FIG. 5(A)

LINEUP OF FIGURE 1 FROM XXXXXXXXXXXX

```
              1                                                          50
Bovneo   ................ .......... .AGTCATATG CTTGTCTTAA AGATTAAGCC 51                                                         100
Bovneo   ATGCATGTCT AAGTATAAGC TTTTATACGG CTAAACTGCG AATGGCTCAT 101                                                         150
Bovneo   TAAAACAGTT ATAGTTTATT TGATGGTCTT TACTACATGG ATAACCGTGG 151                                                         200
Bovneo   TAATTCTATG GCTAATACAT GCGCACATGC CTCTTCCTCT GGAAGGGCAG 201                                                         250
Bovneo   TGTTTATTAG ATACAGAACC AACCCACCTT CCGGTGGTCC TCGGGTGATT 251                                                         300
Bovneo   CATAGTAACC GAACGGATCG CGTTTGACTT CGGTCTGCGA CGGATCATTC 301                                                         350
Bovneo   AAGTTTCTGA CCTATCAGCT TTCGACGGTA CTGTATTGGA CTACCGTGGC 351                                                         400
Bovneo   AGTGACGGGT AACGGGGAAT TAGGGTTCGA TTCCGGAGAG GGAgcctgaG 401                                                         450
Bovneo   AAACGGCTAC CACATCTAAG GAAGGCAGCA GGCGCGcaAA TTACCCAATC 451                                                         500
Bovneo   CTGATTCAGG GAGGTAGTGA CAAGAAATAA CAACACTgGA AATTTCATTT 501                                                         550
Bovneo   CTAGTgATTg GAATgATAGG AATcCAAACC CCTTTCAGAG TAACAATTgg 551                                                         600
Bovneo   aGGGcAAGTC TggTgccagc agccgcggta attccagctc caatagcGta
```

FIG. 5(B)

```
          601                                                        650
Bovneo    TattAAAGTT GTTGCAGTTA AAAAGCTCGT AGTTGGATTt CTGCTGGAAG 651                                                        700
Bovneo    CAGCCAGTCC GCCCTCAGGG GTGTGCACTT GGTGAATTCT AGCATCCTTC 701                                                        750
Bovneo    TGGATTTCTT CACACTTCAT TgtgtgGagt TTtttCCAGG ACTTTTACTT 751                                                        800
Bovneo    TGAGAAAATT AGAGTGTTTC AAGCAGGCTT GTCGCCTTGA AtACTGCAGC 801                                                        850
Bovneo    ATGGAATAAT AAGATAGGAT TTCGGCCCTA TTTTGTTGGT TTCTAGGACT 851                                                        900
Bovneo    GAAGTAATga TTAATAGGGA CGGTTGGGgg CATTCGTATT TAACTGTCAG 901                                                        950
Bovneo    AGGTGAAATT CTTAGATTTG TTAAAGACGA ACTACTGCGA AAGCATTTGC 951                                                       1000
Bovneo    CAAAGATGtT TTcaTTAATc AaGaACGAAa GttaggGGCT CGaAGacgat 1001                                                       1050
Bovneo    CAgataccgt cgtaGTctTa acCATAAACT ATGCCGACTA GAGATAgGaA 1051                                                       1100
Bovneo    AACGtCATGC ttGaCTTCTC CTgCACCTTA TGAGAAATCA AaGtcTttgG 1101                                                       1150
Bovneo    GttcTGGGGG GAgtatGGtC gcaaggctga aacttaAAGG AATTGaCGgA 1151                                                       1200
Bovneo    AGGGCACCAC CAGGCGTGGa gcctgcggCT TAATTTGACT CAACACGGGG
```

FIG. 5(C)

```
        1201                                                 1250
Bovneo  AAACtCACCA GGTCCagaca taggaaggat tgacagattg atagctcttt 1251                                                 1300
Bovneo  cttgattcta tgggtggtgg tgcatggccg ttcttagttg gtggagtgat 1301                                                 1350
Bovneo  ttgtctggtt aattccgtta acgaacgaga ccttaacctg ctaaatagga 1351                                                 1400
Bovneo  tcaggaactt cgtgttcttg tatcacttct tagagggact ttgcgtgtct 1401                                                 1450
Bovneo  aacgcaagga agtttgaggc aataacaggt ctgtgatgcc cttagatgtt 1451                                                 1500
Bovneo  ctgggctgca cGCGCGCTAc actgaTGCAT CCAaCGAGTT TATAaCCTTG 1501                                                 1550
Bovneo  gCCGATAGGT CTAGGTAatC TtGTGAGTAT GCAtCGTGAT GGGgatagaT 1551                                                 1600
Bovneo  TATTGCAaTT ATTAATCTTC AACGAGgaat gcctagtagG CGCAAGTCAG 1601                                                 1650
Bovneo  cAGCTTGCGc cGATTACGTC cCtgCCCttt gtACAcaccg cccgtcgCTC 1651                                                 1700
Bovneo  CTACCGATTG AGTGTTCCGG TGAATTATTC GGACCGTTtT GTGGCGCGTT 1701                                                 1750
Bovneo  CGTGCCCGAA ATGGGAAGTT TTGTGAACCT TAACACTTAG AGGAAGGAGA 1751                                                 1800
Bovneo  AGTCGTAacA aGgTTtCC
```

BOVINE NEOSPORA ISOLATES

This application is a continuation in part of U.S. Ser. No. 08/215,858, Mar. 21, 1994 now abandoned, which is incorporated herein by reference.

BACKGROUND OF THE INVENTION

This invention relates to the diagnosis and prevention of bovine diseases caused by the protozoan parasite, Neospora. The invention specifically relates to isolated cultures of the parasite and nucleic acids and proteins isolated from them.

A distinct pattern of inflammatory lesions, consisting of focal non-suppurative necrotizing encephalitis, non-suppurative myocarditis and myositis have been observed in many aborted bovine fetuses submitted for diagnosis. The pattern of lesions, particularly in the brain, is similar to those seen with *Toxoplasma gondii* infections in sheep. However, cattle have been reported to be resistant to *T. gondii* infection Dubey, *Vet. Parasit.* 22:177–202 (1986). In 1988, a cyst-forming protozoal parasite was first identified by histopathological examination in fetuses (Barr et al., *Vet. Parasit.* 27:354–61 (1990)). This parasite was morphologically similar to Toxoplasma, except that some of the cysts had thick walls, which was more similar to the *Neospora caninum*-like protozoan observed by Thilsted & Dubey (*J. Vet. Diagnos. Invest.* 1:205–9 (1989)) in aborted fetuses from a dairy in New Mexico.

Further studies showed that the protozoal parasites associated with inflammatory lesions in aborted fetuses and neonatal calves in California had ultrastructural and antigenic features that were most similar to *N. caninum* parasites which were originally isolated from dogs (Dubey et al., *JAVMA* 193:1259–63 (1988)). However, differences in the antigenic reactivity of the bovine protozoan and *N. caninum* when tested with a panel of antisera indicated that they may not be the same species (Barr et al., *Vet. Pathol.* 28:110–16 (1991)).

A more complete understanding of the identity and biology of these bovine protozoa requires establishing continuous in vitro cultures of the parasites. Such cultures would also be valuable in the development of diagnostic assays and pharmaceutical compositions for the treatment and prevention of Neospora infections. The present invention addresses these and other needs.

SUMMARY OF THE INVENTION

The present invention provides biologically pure cultures of bovine Neospora. Two such cultures have been deposited with the ATCC and given ATCC Accession No. 75710 (BPA1), and ATCC Accession No. 75711 (BPA6).

The invention also provides methods of detecting the presence of antibodies specifically immunoreactive with a bovine Neospora antigen in a biological sample (e.g., bovine serum). The method comprises contacting the sample with the Neospora antigen, thereby forming a antigen/antibody complex, and detecting the presence or absence of the complex. The Neospora antigen is an isolated Neospora tachyzoite, bradyzoite, or an isolated Neospora protein. In some embodiments, the antigen is immobilized on a solid surface and the complex is detected using a fluorescently labeled anti-bovine antibody.

The invention further provides methods of detecting the presence of Neospora in a biological sample. These methods comprise contacting the sample with an antibody specifically immunoreactive with a Neospora antigen, thereby forming a antigen/antibody complex, and detecting the presence or absence of the complex. The antibody (e.g., a monoclonal antibody) may be immobilized on a solid surface and the complex detected using a second labeled antibody. Typically, the biological sample is bovine fetal neurological tissue.

The methods of the invention also include detecting the presence of Neospora-specific nucleic acids in a biological sample by contacting the sample with a oligonucleotide probe which specifically hybridizes with a target Neospora-specific polynucleotide sequence and detecting the presence or absence of hybridization complexes. The methods may further comprise amplifying the target Neospora-specific polynucleotide sequence.

The invention further provides pharmaceutical composition comprising a pharmaceutically acceptable carrier and an immunogenically effective amount of a bovine Neospora antigen, such as a recombinantly produced bovine Neospora polypeptide.

The pharmaceutical compositions are used in protecting a bovine animal from infection by bovine Neospora. The compositions are preferably administered to a cow or heifer when the animal is breeding. The pharmaceutical composition is usually administered parenterally.

Definitions

"Antibody" refers to an immunoglobulin molecule able to bind to a specific epitope on an antigen. Antibodies can be a polyclonal mixture or monoclonal. Antibodies can be intact immunoglobulins derived from natural sources or from recombinant sources and can be immunoreactive portions of intact immunoglobulins. Antibodies may exist in a variety of forms including, for example, Fv, $F_{ab}$, and $F(ab)_2$, as well as in single chains. Single-chain antibodies, in which genes for a heavy chain and a light chain are combined into a single coding sequence, may also be used.

"Biological sample" refers to any sample obtained from a living or dead organism. Examples of biological samples include biological fluids and tissue specimens. Examples of tissue specimens include fetal brain tissue, spinal cord, and placenta. Examples of biological fluids include blood, serum, plasma, urine, ascites fluid, cerebrospinal fluid and fetal fluid.

A "biologically pure bovine Neospora culture" refers to a continuous in vitro culture of bovine Neospora organisms (e.g. tachyzoites) which is substantially free of other organisms other than the host cells in which Neospora tachyzoites are grown. A culture is substantially free of other organisms if standard harvesting procedures (as described below) result in a preparation which comprises at least about 95%, preferably 99% or more of the organism, e.g., Neospora tachyzoites.

"Bovine Neospora" refers to Neospora or "Neospora-like" protozoans identified in or isolated from bovine tissues and fluids. Typically, the protozoal parasites can be isolated from neurological tissue of aborted bovine fetuses or congenitally infected calves. Exemplary isolates have been deposited with the American Type Culture Collection, as described below.

A bovine Neospora "protein" or "polypeptide" includes allelic variations normally found in the natural population and changes introduced by recombinant techniques. Those of skill recognize that proteins can be modified in a variety of ways including the addition, deletion and substitution of amino acids.

"Nucleic acids" and "polynucleotides", as used herein, may be DNA or RNA. One of skill will recognize that for use in the expression of Neospora proteins or as diagnostic probes, polynucleotide sequences need not be identical and may be substantially identical to sequences disclosed here. In particular, where the inserted polynucleotide sequence is transcribed and translated to produce a functional polypeptide, one of skill will recognize that because of codon degeneracy a number of polynucleotide sequences will encode the same polypeptide.

"Percentage of sequence identity" for polynucleotides and polypeptides is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by computerized implementations of known algorithms (GAP, BESTFIT, FASTA, and TFASTA in the Wisconsin Genetics Software Package, Genetics Computer Group (GCG), 575 Science Dr., Madison, Wis.), or by inspection.

Substantial identity of polynucleotide sequences means that a polynucleotide comprises a sequence that has at least 75% sequence identity, preferably at least 80%, more preferably at least 90% and most preferably at least 95%. Typically, two polypeptides are considered to be substantially identical if at least 40%, preferably at least 60%, more preferably at least 90%, and most preferably at least 95% are identical or conservative substitutions. Sequences are preferably compared to a reference sequence using GAP using default parameters.

Another indication that polynucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically stringent conditions for a Southern blot protocol involve washing at room temperature with a 5×SSC, 0.1% SDS wash.

The phrase "selectively hybridizing to", refers to a hybridization between a probe and a target sequence in which the probe binds substantially only to the target sequence when the target is in a heterogeneous mixture of polynucleotides and other compounds. Such hybridization is determinative of the presence of the target sequence. Although the probe may bind other unrelated sequences, at least 90%, preferably 95% or more of the hybridization complexes formed are with the target sequence.

The phrase "specifically immunoreactive with", when referring to a protein or peptide, refers to a binding reaction between the protein and an antibody which is determinative of the presence of the protein in the presence of a heterogeneous population of proteins and other compounds. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein and are described in detail below.

The phrase "substantially pure" or "isolated" when referring to a Neospora peptide or protein, means a chemical composition which is free of other subcellular components of the Neospora organism. Typically, a monomeric protein is substantially pure when at least about 85% or more of a sample exhibits a single polypeptide backbone. Minor variants or chemical modifications may typically share the same polypeptide sequence. Depending on the purification procedure, purities of 85%, and preferably over 95% pure are possible. Protein purity or homogeneity may be indicated by a number of means well known in the art, such as polyacrylamide gel electrophoresis of a protein sample, followed by visualizing a single polypeptide band on a polyacrylamide gel upon silver staining. For certain purposes high resolution will be needed and HPLC or a similar means for purification utilized.

BRIEF DESCRIPTION OF THE DRAWINGS

FIG. 5 shows the nucleotide sequence (SEQ ID NO.:1) of DNA encoding nuclear small subunit ribosomal RNA isolated from the cultures of the invention.

DESCRIPTION OF THE PREFERRED EMBODIMENTS

Figure 1:
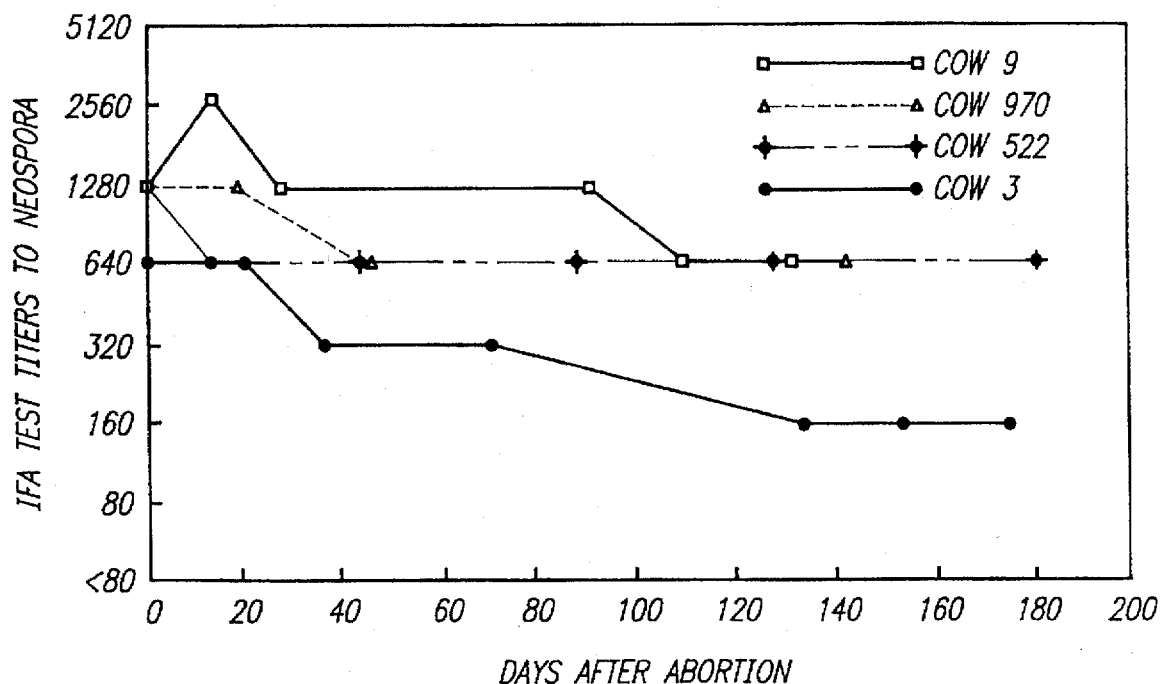
FIG. 1 shows indirect fluorescent antibody (IFA) titers of serial samples from four cows that aborted Neospora-infected fetuses.

The present invention provides Neospora cultures isolated from cattle. The cultures are useful in a variety of applications including the production of nucleic acids or proteins for diagnostic assays and the preparation of immunogenic proteins for use in vaccine compositions.

Neospora tachyzoite cultures of the invention have been deposited with the American Type Culture Collection, Rockville, Md. on Mar. 17, 1994 and given Accession Numbers 75710 (BPA1) and 75711 (BPA6).

These isolates were obtained from tissue homogenates of brain and/or spinal cord of an aborted bovine fetus and congenitally infected calves. Immunohistochemistry was used to identify the tachyzoite and/or cysts associated with lesions in the tissues of these fetuses and calves as Neospora parasites prior to isolation. Tachyzoite stages of the isolates were grown in stationary monolayer cultures of bovine fetal trophoblasts, aortic endothelial cells and/or macrophages. Electron microscopic studies were used to characterize the ultrastructural features of the BPA1 isolate. Antigenically, tachyzoites of 5 separate isolates react strongly with antisera to Neospora and show little or no reactivity with antisera to *Toxoplasma gondii* or *Hammondia hammondi*. Based on these ultrastructural and antigenic characteristics, these parasites can be distinguished from the most closely related and morphologically similar genera of protozoa, Toxoplasma, Hammondia and Sarcocystis.

In addition, partial sequences (500–550 base pairs) of the 5' end of the nuclear small subunit (nss)-rRNA gene for three of the bovine Neospora isolates (BPA1, BPA3 and BPA5) have been obtained and shown to be identical. The more complete 1.8 kilobase sequence of the nss-rRNA gene of the BPA1 isolate was obtained and compared to the sequences for this gene in other coccidial parasites. Alignment of these sequences with published sequences of *Neospora caninum, Cryptosporidium parvum, Sarcocystis muris* and *Toxoplasma gondii* showed that the bovine Neospora isolate is genotypically unique.

As explained in detail below, the isolates are used to develop a variety of diagnostic assays as well as pharmaceutical compositions for treatment and prevention of infection.

Preparation of Neospora polypeptides and nucleic acids

Standard protein purification techniques can be used to isolate proteins from the tachyzoites or bradyzoites derived from the cultures provided here. Such techniques include selective precipitation with such substances as ammonium sulfate, column chromatography, immunopurification methods, and the like. See, for instance, R. Scopes, *Protein Purification: Principles and Practice*, Springer-Verlag: New York (1982).

Using standard immunoblot techniques 11 proteins with molecular weights of approximately 106, 49.5, 48, 33, 32.5, 30, 28, 26, 19, 18 and 17 kilodaltons (kd) have been identified. All of these proteins are specifically recognized by antibodies from Neospora infected cattle. Standard protein purification methods can be used to purify these proteins and produce polyclonal or monoclonal antibodies for use in diagnostic methods described below. Two of these antigens (approximately 106 and 19 kd) have been shown to be useful in enzyme-linked immunoassays (ELISA) for the detection of Neospora-specific antibodies in infected cattle.

Rather than extract the proteins directly from cultured tachyzoites, nucleic acids derived from the cultures can be used for recombinant expression of the proteins. In these methods, the nucleic acids encoding the proteins of interest are introduced into suitable host cells, followed by induction of the cells to produce large amounts of the protein. The invention relies on routine techniques in the field of recombinant genetics, well known to those of ordinary skill in the art. A basic text disclosing the general methods of use in this invention is Sambrook et al., *Molecular Cloning, A Laboratory Manual*, Cold Spring Harbor Publish., Cold Spring Harbor, N.Y. 2nd ed. (1989).

Nucleic acids for use as diagnostic oligonucleotide probes or for the recombinant expression of proteins can be isolated using a number of techniques. For instance, portions of proteins isolated from the cultures discussed above can be sequenced and used to design degenerate oligonucleotide probes to screen a cDNA library. Amino acid sequencing is performed and oligonucleotide probes are synthesized according to standard techniques as described, for instance, in Sambrook et al., supra. Alternatively, oligonucleotide probes useful for identification of desired genes can also be prepared from conserved regions of related genes in other species.

Alternatively, polymerase chain reaction technology (PCR) can be used to amplify nucleic acid sequences of the desired gene directly from mRNA, from cDNA, from genomic libraries or cDNA libraries. Polymerase chain reaction (PCR) or other in vitro amplification methods may also be useful, for example, to clone nucleic acid sequences that code for proteins to be expressed, to make nucleic acids to use as probes for detecting the presence of the mRNA in physiological samples, for nucleic acid sequencing, or for other purposes. For a general overview of PCR see *PCR Protocols: A Guide to Methods and Applications*. (Innis, M., Gelfand, D., Sninsky, J. and White, T., eds.), Academic Press, San Diego (1990).

Standard transfection methods are used to produce prokaryotic, mammalian, yeast or insect cell lines which express large quantities of the desired polypeptide, which is then purified using standard techniques. See, e.g., Colley et al., *J. Biol. Chem.* 264:17619–17622, 1989; and Guide to Protein Purification, supra.

The nucleotide sequences used to transfect the host cells can be modified to yield Neospora polypeptides with a variety of desired properties. For example, the polypeptides can vary from the naturally-occurring sequence at the primary structure level by amino acid, insertions, substitutions, deletions, and the like. These modifications can be used in a number of combinations to produce the final modified protein chain.

The amino acid sequence variants can be prepared with various objectives in mind, including facilitating purification and preparation of the recombinant polypeptide. The modified polypeptides are also useful for modifying plasma half life, improving therapeutic efficacy, and lessening the severity or occurrence of side effects during therapeutic use. The amino acid sequence variants are usually predetermined variants not found in nature but exhibit the same immunogenic activity as naturally occurring protein. In general, modifications of the sequences encoding the polypeptides may be readily accomplished by a variety of well-known techniques, such as site-directed mutagenesis (see, Gillman and Smith, *Gene* 8:81–97, 1979) and Roberts, S. et al., *Nature* 328:731–734, 1987). One of ordinary skill will appreciate that the effect of many mutations is difficult to predict. Thus, most modifications are evaluated by routine screening in a suitable assay for the desired characteristic. For instance, the effect of various modifications on the ability of the polypeptide to elicit a protective immune response can be easily determined using in vitro assays. For instance, the polypeptides can be tested for their ability to induce lymphoproliferation, T cell cytotoxicity, or cytokine production using standard techniques.

The particular procedure used to introduce the genetic material into the host cell for expression of the polypeptide is not particularly critical. Any of the well known procedures for introducing foreign nucleotide sequences into host cells may be used. These include the use of calcium phosphate transfection, spheroplasts, electroporation, liposomes, microinjection, plasmid vectors, vital vectors and any of the other well known methods for introducing cloned genomic DNA, cDNA, synthetic DNA or other foreign genetic material into a host cell (see Sambrook et al., supra). It is only necessary that the particular procedure utilized be capable of successfully introducing at least one gene into the host cell which is capable of expressing the gene.

Any of a number of well known cells and cell lines can be used to express the polypeptides of the invention. For instance, prokaryotic cells such as *E. coli* can be used. Eukaryotic cells include, yeast, Chinese hamster ovary (CHO) cells, COS cells, and insect cells.

The particular vector used to transport the genetic information into the cell is also not particularly critical. Any of the conventional vectors used for expression of recombinant proteins in prokaryotic and eukaryotic cells may be used. Expression vectors for mammalian cells typically contain regulatory elements from eukaryotic viruses.

The expression vector typically contains a transcription unit or expression cassette that contains all the elements required for the expression of the polypeptide DNA in the host cells. A typical expression cassette contains a promoter operably linked to the DNA sequence encoding a polypeptide and signals required for efficient polyadenylation of the transcript. The term "operably linked" as used herein refers to linkage of a promoter upstream from a DNA sequence such that the promoter mediates transcription of the DNA sequence. The promoter is preferably positioned about the same distance from the heterologous transcription start site as it is from the transcription start site in its natural setting. As is known in the art, however, some variation in this distance can be accommodated without loss of promoter function.

Following the growth of the recombinant cells and expression of the polypeptide, the culture medium is harvested for purification of the secreted protein. The media are typically clarified by centrifugation or filtration to remove cells and cell debris and the proteins are concentrated by adsorption to any suitable resin or by use of ammonium sulfate fractionation, polyethylene glycol precipitation, or by ultrafiltration. Other routine means known in the art may be equally suitable. Further purification of the polypeptide can be accomplished by standard techniques, for example, affinity chromatography, ion exchange chromatography, sizing chromatography, $His_6$ tagging and Ni-agarose chromatography (as described in Dobeli et al. *Mol. and Biochem. Parasit.* 41:259–268 (1990)), or other protein purification techniques to obtain homogeneity. The purified proteins are then used to produce pharmaceutical compositions, as described below.

An alternative method of preparing recombinant polypeptides useful as vaccines involves the use of recombinant viruses (e.g., vaccinia). Vaccinia virus is grown in suitable cultured mammalian cells such as the HeLA S3 spinner cells, as described by Mackett, Smith and Moss, "*The construction and characterization of Vaccinia Virus Recombinants Expressing Foreign Genes*" in "*DNA cloning Vol. II. A practical approach*", Ed. D. M. Glover, IRL Press, Oxford, pp 191–211.

Antibody Production

The isolated proteins or cultures of the present invention can be used to produce antibodies specifically reactive with Neospora antigens. If isolated proteins are used, they may be recombinantly produced or isolated from Neospora cultures. Synthetic peptides made using the protein sequences may also be used.

Methods of production of polyclonal antibodies are known to those of skill in the art. In brief, an immunogen, preferably a purified protein, is mixed with an adjuvant and animals are immunized. When appropriately high titers of antibody to the immunogen are obtained, blood is collected from the animal and antisera is prepared. Further fractionation of the antisera to enrich for antibodies reactive to Neospora proteins can be done if desired. (See Harlow and Lane, *Antibodies: A Laboratory Manual*, Cold Spring Harbor Pubs., N.Y. (1988)).

Polyclonal antisera to the BPA1 and BPA3 isolates have been produced and evaluated. The polyclonal antisera are used to identify and characterize Neospora tachyzoite and bradyzoite stages in the tissues of infected animals using, for instance, immunoperoxidase test procedures described in Anderson et al. *JAVMA* 198:241 (1991) and Barr et al. *Vet. Pathol.* 28:110–116 (1991).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

For instance, the BPA1 isolate has been used to immunize mice to obtain sensitized B cells for hybridoma production. Using these cells, monoclonal antibodies to the 48 kd and 70 kd Neospora proteins have been obtained. The monoclonal antibodies produced are used, for instance, in ELISA diagnostic tests, immunohistochemical tests, for the in vitro evaluation of parasite invasion, to select candidate antigens for vaccine development, protein isolation, and for screening genomic and cDNA libraries to select appropriate gene sequences.

Diagnosis of Neospora infections

The present invention also provides methods for detecting the presence or absence of Neospora in a biological sample. For instance, antibodies specifically reactive with Neospora can be detected using either proteins or the isolates described here. The proteins and isolates can also be used to raise specific antibodies (either monoclonal or polyclonal) to detect the antigen in a sample. In addition, the nucleic acids disclosed and claimed here can be used to detect Neospora-specific sequences using standard hybridization techniques. Each of these assays is described below.

A. Immunoassays

For a review of immunological and immunoassay procedures in general, see *Basic and Clinical Immunology* 7th Edition (D. Stites and A. Terr ed.) 1991. The immunoassays of the present invention can be performed in any of several configurations, which are reviewed extensively in *Enzyme Immunoassay*, E. T. Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B. V. Amsterdam (1985). For instance, the proteins and antibodies disclosed here are conveniently used in ELISA, immunoblot analysis and agglutination assays. Particularly preferred assay formats include the indirect fluorescent antibody assay as described in Example 2.

In brief, immunoassays to measure anti-Neospora antibodies or antigens can be either competitive or noncompetitive binding assays. In competitive binding assays, the sample analyte (e.g., anti-Neospora antibodies) competes with a labeled analyte (e.g., anti-Neospora monoclonal antibody) for specific binding sites on a capture agent (e.g., isolated Neospora protein) bound to a solid surface. The concentration of labeled analyte bound to the capture agent is inversely proportional to the amount of free analyte present in the sample.

Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means.

A number of combinations of capture agent and labelled binding agent can be used. For instance, an isolated Neospora protein or culture can be used as the capture agent and labelled anti-bovine antibodies specific for the constant region of bovine antibodies can be used as the labelled binding agent. Goat, sheep and other non-bovine antibodies specific for bovine immunoglobulin constant regions (e.g. γ or μ) are well known in the art. Alternatively, the anti-bovine antibodies can be the capture agent and the antigen can be labelled.

Various components of the assay, including the antigen, anti-Neospora antibody, or anti-bovine antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC or polystyrene) or a bead. The desired component may be covalently bound or noncovalently attached through nonspecific bonding.

Alternatively, the immunoassay may be carried out in liquid phase and a variety of separation methods may be employed to separate the bound labeled component from the unbound labelled components. These methods are known to those of skill in the art and include immunoprecipitation, column chromatography, adsorption, addition of magnetizable particles coated with a binding agent and other similar procedures.

An immunoassay may also be carried out in liquid phase without a separation procedure. Various homogeneous immunoassay methods are now being applied to immunoassays for protein analytes. In these methods, the binding of the binding agent to the analyte causes a change in the signal emitted by the label, so that binding may be measured without separating the bound from the unbound labelled component.

Western blot (immunoblot) analysis can also be used to detect the presence of antibodies to Neospora in the sample. This technique is a reliable method for confirming the presence of antibodies against a particular protein in the sample. The technique generally comprises separating proteins by gel electrophoresis on the basis of molecular weight, transferring the separated proteins to a suitable solid support, (such as a nitrocellulose filter, a nylon filter, or derivatized nylon filter), and incubating the sample with the separated proteins. This causes specific target antibodies present in the sample to bind their respective proteins. Target antibodies are then detected using labeled anti-bovine antibodies.

The immunoassay formats described above employ labelled assay components. The label can be in a variety of forms. The label may be coupled directly or indirectly to the desired component of the assay according to methods well known in the art. A wide variety of labels may be used. The component may be labelled by any one of several methods. Traditionally a radioactive label incorporating $^{3}H$, $^{125}I$, $^{35}S$, $^{14}C$, or $^{32}P$ was used. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see U.S. Pat. No. 4,391,904, which is incorporated herein by reference.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

Some assay formats do not require the use of labelled components. For instance, agglutination assays can be used to detect the presence of the target antibodies. In this case, antigen-coated particles are agglutinated by samples comprising the target antibodies. In this format, none of the components need be labelled and the presence of the target antibody is detected by simple visual inspection.

B. Detection of Neospora nucleic acids

As noted above, this invention also embraces methods for detecting the presence of Neospora DNA or RNA in biological samples. These sequences can be used to detect all stages of the Neospora life cycle (e.g., tachyzoites, bradyzoites, and oocysts) in biological samples from both the bovine host and the definitive host. A variety of methods of specific DNA and RNA measurement using nucleic acid hybridization techniques are known to those of skill in the art. See Sambrook et al., supra.

One method for determining the presence or absence of Neospora DNA in a sample involves a Southern transfer. Briefly, the digested DNA is run on agarose slab gels in buffer and transferred to membranes. In a similar manner, a Northern transfer may be used for the detection of Neospora mRNA in samples of RNA. Hybridization is carried out using labelled oligonucleotide probes which specifically hybridize to Neospora nucleic acids. Labels used for this purpose are generally as described for immunoassays. Visualization of the hybridized portions allows the qualitative determination of the presence or absence of Neospora genes.

A variety of other nucleic acid hybridization formats are known to those skilled in the art. For example, common formats include sandwich assays and competition or displacement assays. Hybridization techniques are generally described in *"Nucleic Acid Hybridization, A Practical Approach,"* Ed. Hades, B. D. and Higgins, S. J., IRL Press, 1985; Gall and Pardue (1969), *Proc. Natl. Acad. Sci., U.S.A.,* 63:378–383; and John, Burnsteil and Jones (1969) *Nature,* 223:582–587.

Sandwich assays are commercially useful hybridization assays for detecting or isolating nucleic acid sequences. Such assays utilize a "capture" nucleic acid covalently immobilized to a solid support and labelled "signal" nucleic acid in solution. The biological sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems.

An alternative means for detecting Neospora nucleic acids is in situ hybridization. In situ hybridization assays are well known and are generally described in Angerer, et al., *Methods Enzymol.*, 152:649–660 (1987). In situ hybridization assays use cells or tissue fixed to a solid support, typically a glass slide. If DNA is to be probed, the cells are denatured with heat or alkali. The cells are then contacted with a hybridization solution at a moderate temperature to permit annealing of labelled Neospora specific probes. The probes are preferably labelled with radioisotopes or fluorescent reporters.

Exemplary nucleic acid sequences for use in the assays described above include sequences from the nss-rRNA sequences disclosed here. For instance, the primer and probe sequences disclosed in Example 4 can be used to amplify and identify nucleic acids of bovine Neospora in blood, cerebrospinal fluid and fetal fluids, as well as in frozen or formalin-fixed tissue. These primers are particularly useful for the diagnosis of neosporosis and identification of the source of Neospora parasite stages (tachyzoites, bradyzoites and oocysts) in various animal hosts.

Pharmaceutical Compositions comprising Neospora

A pharmaceutical composition prepared using anti-Neospora monoclonal antibodies or fragments thereof as well as Neospora proteins or their immunogenic equivalents can be used in a variety of pharmaceutical preparations for the treatment and/or prevention of Neospora infections.

The pharmaceutical compositions are typically used to vaccinate cattle, sheep, goats and other animals infected by Neospora. The compositions of the invention can also be used to treat the definitive host to prevent the shedding of oocysts and subsequent transfer to cattle. The compositions for administration to either cattle or the definitive host can comprise tachyzoite and/or bradyzoite antigens.

An attenuated Neospora vaccine can only be used in the absence of a risk of human infection should the milk or tissues of immunized animals be consumed. Thus, preferred vaccines are subunit vaccines that elicit antibody and cell-mediated immunity (CMI) to antigens of bovine Neospora. Experimental evidence indicates that CMI is an important component of the protective immune response in cattle. A variety of methods for evaluating the specificity of the helper and cytotoxic T cell response to selected antigens in vitro can be used. In addition, as demonstrated below, cows infected using culture-derived tachyzoites mount a protective immune response and prevent transplacental infection of the fetus.

The vaccines of the invention are typically administered orally or parenterally, usually intramuscularly or subcutaneously. For parenteral administration, the antigen may be combined with a suitable carrier. For example, it may be administered in water, saline or buffered vehicles with or without various adjuvants or immunomodulating agents such as aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid, *Bordetella pertussis*, and the like. Such adjuvants are available commercially from various sources, for example, Merck Adjuvant 6 (Merck and Company, Inc., Rahway, N.J.). Other suitable adjuvants are MPL+TDM Emulsion (RIBBI Immunochem Research Inc. U.S.A.). Other immuno-stimulants include interleukin 1, interleukin 2 and interferon-gamma. These proteins can be provided with the vaccine or their correspondifunctionac sequence provided as a functional operon with a recombinant vaccine system such as vaccinia virus. The proportion of antigen and adjuvant can be varied over a broad range so long as both are present in effective amounts.

Vaccine compositions of the invention are administered to a cattle, sheep, or goats susceptible to or otherwise at risk of infection to elicit an immune response against the antigen and thus enhance the patient's own immune response capabilities. Such an amount is defined to be an "immunogenically effective amount." In this use, the precise amounts depend on the judgement of the prescribing veterinarian and would include consideration of the patient's state of health and weight, the mode of administration, the nature of the formulation, and the like. Generally, on a per-dose basis, the concentration of the Neospora antigen can range from about 1 µg to about 100 mg per bovine host. For administration to cattle, a preferable range is from about 100 µg to about 1 mg per unit dose. A suitable dose size is about 1–10 ml, preferably about 1.0 ml. Accordingly, a typical dose for subcutaneous injection, for example, would comprise 1 to 2 ml containing 0.1 to 10 mg of antigen.

A variety of vaccination regimens may be effective in immunizing cattle and other animals. Preferably, female cattle (heifers and cows) are vaccinated just prior to or at the time of breeding so as to prevent abortion and reduce the possibility of congenital infections. A second immunization will be given 2–4 weeks after initial immunization. Calves and adult males may also be vaccinated, if desired. Animals that have been previously exposed to Neospora or have received colostral antibodies from the mother may require booster injections. The booster injection is preferably timed to coincide with times of maximal challenge and/or risk of abortion. Different immunization regimes may be adopted depending on the judgement of the veterinarian.

Vaccines of the invention may comprise a crude extract of Neospora tachyzoites, bradyzoites or other stages. Chemically fixed parasites or cells can also be used. As noted above, preferred vaccines comprise partially or completely purified Neospora protein preparations. The antigen produced by recombinant DNA technology is preferred because it is more economical than the other sources and is more readily purified in large quantities.

In addition to use in recombinant expression systems, the isolated Neospora gene sequences can also be used to transform viruses that transfect host cells in animals. Live attenuated viruses, such as vaccinia or adenovirus, are convenient alternatives for vaccines because they are inexpensive to produce and are easily transported and administered.

Suitable viruses for use in the present invention include, but are not limited to, pox viruses, such as capripox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the DNA's encoding the Neospora protein or fragments thereof into plasmids so that they are flanked by viral sequences on both sides. The DNA's encoding Neospora polypeptides are then inserted into the virus genome through homologous recombination.

Preferentially, a viral vaccine using recombinant vaccinia virus is used. A vaccine prepared utilizing the gene encoding the Neospora protein incorporated into vaccinia virus would comprise stocks of recombinant virus where the gene encoding the Neospora protein is integrated into the genome of the virus in a form suitable for expression of the gene.

EXAMPLES

Example 1

This example describes the isolation and in vitro cultivation of Neospora from aborted bovine fetuses. The isolation of these 2 cultures (BPA1 and BPA2) is described in Conrad et al. *Parasitol.* 106:239–249 (1993). Additional cultures (BPA3–6) were also isolated using the same technique, except that 1 ml (instead of 2 ml) of brain or spinal cord homogenate was trypsinized and then incubated for 2–4 hours, rather than overnight, on the cell monolayer. In addition, the bovine aortic endothelial cell line (CPAE: American Tissue Culture Collection #CCL209) was found to be the best cell monolayer for the cultivation of bovine Neospora. One of these cultures (BPA6) has been shown to induce bradyzoite cysts in mice.

MATERIALS AND METHODS

Pathological examination and immunohistochemistry of fetal tissues

Aborted bovine fetuses submitted to the California Veterinary Diagnostic Laboratory System were necropsied using standard techniques. The brains from fetuses suspected of having protozoal infections were removed aseptically from the cranium. One half of the brain was placed in sterile saline (0–85% w/v) containing 1000 U/ml penicillin G and 100 µg/ml streptomycin (antibiotic saline) and stored at 4° C. until a diagnosis of protozoal infection was confirmed, at which time the brain could be processed for in vitro cultivation. Multiple tissues, including portions of the brain, liver, kidney, heart, lung, spleen, gastrointestinal tract, skeletal muscle, adrenal, trachea and thymus, were collected from each fetus and fixed in 10% neutral buffered formalin for 24 h. Fixed tissues were trimmed, embedded in paraffin, sectioned, stained with hematoxylin and eosin, and examined by light microscopy for the presence of lesions and parasites, as previously described (Barr et al. 1990 *Vet. Pathol.* 27:354–61).

Fetuses with multifocal microgliosis and/or necrosis in the brain, suggesting protozoal infection, were further examined by immunohistochemistry for the presence of parasites in brain tissue sections using an avidin-biotin peroxidase complex procedure (Vector Laboratories, Burlingame, Calif., U.S.A.) with anti-rabbit serum to detect tissue-binding of rabbit polyclonal anti-*N. caninum* serum. The immunoperoxidase method employed was basically as described previously (Barr et al. 1991 *J. Vet. Diag. Invest.* 3:39–46) except that tissue sections were processed using a microprobe system (FisherBiotech, Pittsburgh, Pa., U.S.A.) and Probe-On glass slides (FisherBiotech). Aminoethylcarbazole (A. E. C. Substrate System, Dako, Santa Barbara, Calif., U.S.A.) was the chromogen.

Parasites in the tissue sections of brains from the 66th and 93rd fetus (hereafter referred to as fetus 66 and 93) were further characterized by the same immunohistochemical procedure to test their reactivity with antisera to additional apicomplexan protozoal parasites. Tissue sections were incubated at room temperature for 1 h with optimal dilutions of the following antisera: 1:1000 dilution of antiserum to *N. caninum* tachyzoites (Lindsay & Dubey, 1989 *Am. J. Vet. Res.* 50:1981–3), 1:50 dilution of antiserum to *Hammondia hommondi* tissue cysts and 4 different antisera to *T. gondii* (Tg1-4). Antiserum Tg1 was produced by the infection of a rabbit with live sporulated oocysts of the ME-49 strain (Lindsay & Dubey, supra) of *T. gondii* and used at a 1:400 dilution. *Toxoplasma gondii* antiserum Tg2 (Dr J. C. Boothroyd, Stanford University) was produced by immunization of a rabbit with a tachyzoite lysate of the RH strain of *T. gondii* and was used at a dilution of 1:300. Antisera Tg3 (BioGenex Laboratories, Dublin, Calif., U.S.A.) and Tg4 (I. C. N. Immunobiologicals, Lisle, Ill., U.S.A.) were developed by immunizing rabbits with tachyzoites of the RH and H44 strains, respectively. Antiserum Tg3 was applied as supplied by the manufacturer and Tg4 was used at a 1:80 dilution. The optimal dilution chosen for each antiserum produced a strongly positive reaction against the respective positive control parasite with no appreciable non-specific, background staining. Control tissues consisted of paraffin-embedded sections of murine brain with *N. caninum* tachyzoites, murine brain with *T. gondii* cysts, murine spleen with *T. gondii* tachyzoites, murine skeletal muscle with *H. hammondi* cysts and bovine tongue with *Sarcocystis cruzi* cysts (Barr et al. 1991 *Vet. Path.* 28:110–116).

Parasite cultures

Stationary monolayer cultures of bovine cardiopulmonary aortic endothelial cells (CPAE: ATCC #CCL209) and M617 bovine macrophages (Speer et al. 1985 *Infect. and Immun.* 50:566–71) were maintained in Dulbecco's Minimum Essential Medium (DMEM:GIBCO Laboratories, Grand Island, N.Y., U.S.A.) supplemented with 10% (v/v) heat-inactivated fetal bovine serum (FBS) or heat-inactivated adult equine serum (HS), 2 mM L-glutamine, 50 U/ml penicillin and 50 µg/ml streptomycin (DMEM-FBS or DMEM-HS). Bovine fetal trophoblast cells (87-3) were grown is previously described by Munson et al. 1988 *J. Tissue Cult. Methods* 11:123–8) in DMEM supplemented with 10% (v/v) FBS, 5 µg/ml transferrin, 5 µg/ml insulin, 5 ng/ml selenium, 10 ng/ml epidermal growth factor, 100 µg/ml streptomycin, 100 U/ml penicillin and 0.25 µg/ml amphotericin B (DMEM-FBS*). Control cultures of *T. gondii* (RH strain provided by Dr J. Boothroyd) and *N. caninum* (NC1; Dubey et al. 1988 *J Am Vet Med Assoc* 193:1259–1263) were maintained in the CPAE and M617 monolayer cultures. Parasite-infected and uninfected monolayer cultures were maintained in 25 or 75 cm² flasks incubated at 37° C. with 5% $CO_2$. Culture medium was changed 3 times weekly. Established parasite cultures were passaged to uninfected monolayers when 70–90% of cells were infected. To passage parasites, the infected monolayer was removed from the flask by scraping into the media and passed 3 times through a 25-gauge needle to disrupt the cells. The cell suspension was then diluted from 1:2 to 1:8 in fresh complete media and added to a confluent, uninfected monolayer.

After protozoal infection was confirmed by histology, fetal brain tissue that was stored at 4° C. for a variable period of time in antibiotic saline was processed for in vitro cultivation. In all cases where isolates were obtained in vitro, tissue cysts were seen in tissue sections of bovine fetal brain. Half of the fetal brain in approximately 25 ml of antibiotic saline was ground with a pestle and mortar and filtered through sterile gauze. Aliquots of 2 ml of brain homogenate were placed in 10 ml of 0.05% (v/v) trypsin and incubated at 37° C. for 1 h. After trypsin digestion, the material was pelleted by centrifugation at 600 g for 10 min. The supernatant was discarded and the pellet was resuspended in 1–3 ml of either DMEM-HS or DMEM-FBS. Brain from fetus 66 was prepared for culture 48 h after submission and 1 ml of trypsinized brain suspension was dispensed into a 25 cm² flask of bovine 87-3 trophoblast cells. Brain from fetus 93 was processed 10 days after submission when half of the trypsinized brain was placed in a 25 cm² flask of 87-3 trophoblast cells and the remainder in a 75 cm² flask of endothelial cells. After incubation overnight, the brain suspension from both fetuses was removed from the flask and the monolayers were washed 3 times with the appropriate media before adding 5–10 ml of fresh media. Cultures were maintained as described above and examined with an inverted microscope for the presence of parasites.

Immunohistochemistry of tachyzoites in vitro

Antigenic reactivity of the two in vitro isolates from aborted bovine fetuses was compared to that of tachyzoites from control cultures of *T. gondii* and *N. caninum*. Tachyzoites of each isolate were harvested during logarithmic growth by scraping the infected CPAE monolayer from a 25 cm$^2$ tissue culture flask. Monolayer cells were disrupted by repeated passage through a 25-gauge needle. The suspension was passed through a 5 µm filter to remove cellular debris and pelleted by centrifugation at 1500 g for 10 min. After removing the supernatant fraction, the pelleted tachyzoites of each isolate were resuspended in DMEM-HS and inoculated into each of the wells on two 4-chambered tissue culture slides (Lab-Tek, Nunc, Naperville, Ill., U.S.A.). Each of the 4 chambers on these slides were seeded 24–48 h prior to parasite inoculation with CPAE cells so that the monolayers were 60–80% confluent at the time of infection. The appropriate slides were inoculated with the slower growing bovine fetal isolates first to allow the parasites to grow for 48 h, whereas the isolates of *T. gondii* and *N. caninum* were cultivated on slides for 24 h before being processed for immunohistochemical evaluation.

To prepare the parasite cultures for immunohistochemistry, culture supernatants were removed with monolayers remaining adherent to glass slides. These slides were fixed in 100% methanol (4° C.) for 10 min and allowed to air dry completely before being washed 3 times for 5 min each in physiologically buffered saline (PBS:pH 7–2), incubated for 10 min in 3% (v/v) hydrogen peroxide in methanol, washed again 3 times for 5 min each in PBS and incubated for 30 min with 20% goat serum to block non-specific antibody binding sites. Each slide was then incubated for 1 h with 3 wells containing different primary antiserum and 1 well serving as a negative control with a pre-infection rabbit serum. The optimal antisera dilutions were selected to produce a strongly positive reaction against the homologous culture-derived antigen with no appreciable non-specific, background staining. The dilutions of antisera used for staining parasites in vitro were 1:3000 for *N. caninum*, 1:800 for Tg1, 1:40 for Tg2, 1:1 for Tg3, 1:2000 for Tg4 and 1:50 for *H. hommondi*. Slides were washed 3 times for 5 min each in PBS and the secondary antibody and conjugate were applied as described above for the tissue sections except that the slides were processed manually and the chromogen was applied for only 2 min.

RESULTS

The first parasite isolate (BPA1) was obtained from fetus 66 which was estimated to be approximately 4 months gestational age and in relatively good postmortem condition at the time of necropsy. Significant gross lesions were restricted to focal epicardial petechiae. On histological examination there were infrequent, random, small foci of gliosis and 5 protozoal cysts were seen in sections of the fetal brain. The tissue cysts ranged from 8 to 10 µm in diameter and had distinct, thin walls (<1 µm) surrounding at least 25–40 closely packed bradyzoites. In addition there were scattered mononuclear inflammatory cell infiltrates in the heart, portal tracts of the liver and throughout the renal cortex. In the lung, macrophages and neutrophils were present within alveolar septa, adjacent to bronchioles and free in the lumen of bronchioles and alveoli. *Escherichia coli* and *Proteus* spp. were isolated from the lung, liver, spleen and abomasal contents of this fetus.

The second isolate (BPA2) was obtained from fetus 93 which had an estimated gestational age of 6 months and was mildly autolyzed. Histological examination revealed infrequent random foci of gliosis in the brain with adjacent capillaries that had prominent hypertrophied endothelium. There was also a mild diffuse meningeal infiltrate of mononuclear cells, consisting predominantly of lymphocytes with occasional plasma cells. Four randomly located protozoal tissue cysts were found in the brain; one being located adjacent to a focus of gliosis. The cysts were 8–13 µm in diameter with at least 25–50 bradyzoites. Two of the cysts had thick (1–2 µm) walls. Focal, mixed mononuclear inflammatory cell infiltrates were also present in skeletal muscle and in the renal cortex.

Table 1 summarizes the immunoreactivity of protozoal tissue cysts in the brains of fetus 66 and fetus 93 with different polyclonal antisera and compares these antigenic reactions to those of *N. caninum*, *T. gondii*, *H. hommondi* and *S. cruzi*. The protozoal cysts in fetuses 66 and 93 reacted most strongly to *N. caninum* antiserum and had weaker reactions to *H. hommondi* antiserum. With both antisera, staining was predominantly to the cyst wall with some staining of zoites within the cysts. Overall, the reactivity of cysts in the two bovine fetuses was more similar to the reactivity of *N. caninum* tachyzoites than to that of *T. gondii* tachyzoites or cysts, *H. hommondia* cysts or *S. cruzi* cysts.

TABLE 1

Reactivity of tissue cysts and tachyzoites with rabbit polyclonal antisera against different parasites in an immunoperoxidase test

| Parasite antigen | Tissue | Neospora caninum | Hammondia hammondi | Toxoplasma gondii | | | |
|---|---|---|---|---|---|---|---|
| | | | | Tg1 | Tg2 | Tg3 | Tg4 |
| Fetus 66 cysts | Bovine brain | ++* | ++* | ± | – | – | – |
| Fetus 93 cysts | Bovine brain | ++* | +* | – | – | – | – |
| *Neospora caninum* tachyzoites | Mouse brain | +++ | – | ++ | – | – | – |
| *Toxoplasma gondii* tachyzoites | Mouse spleen | – | ++ | +++ | +++ | ± | ± |
| *Toxoplasma gondii* cysts | Mouse brain | + | +++ | +++ | + | ++ | ++ |
| *Hammondia hammondi* cysts | Mouse muscle | ± | +++ | +++ | – | + | ++ |
| *Sarcocystis cruzi* cysts | Bovine muscle | – | – | – | – | – | – |

*Primarily cyst wall staining.

In approximately 14 months, over 100 fetuses were submitted specifically as protozoal abortion suspects from dairies in California. Parasite isolations were attempted with brain from the 49 fetuses which had Neospora-like protozoa identified by immunohistochemistry. The first evidence of parasite growth in these cultures was detected in the 87-3 cell line 34 days after inoculation of brain tissue from fetus 66 (isolate BAP1). The next successful in vitro isolation was apparent when tachyzoites were first observed in 87-3 and CPAE cultures on day 15 after inoculation with brain tissue from fetus 93 (isolate BPA2). In cultures of both isolates, parasites first appeared as small clusters of intracellular tachyzoites in pairs or random groups. Extracellular tachyzoites were seen escaping from the bovine cell monolayers and moving by gliding and twisting in the culture medium. On Giemsa-stained smears of infected monolayers, extracellular tachyzoites were 1.5–2.5 μm wide at the nucleus and 6–8 μm long. The number of tachyzoite clusters and number of tachyzoites in each cluster increased gradually in the cultures as they became established with continuous parasite growth. Generally, parasite clusters contained approximately 10–100 tachyzoites. Growth of both isolates was maintained in cultures of 87-3, CPAE, or M617. However, the best growth was observed in the 87-3 and CPAE cultures. Within 2–3 months of establishment, the cultures were passaged weekly whenever approximately 80–95% of the bovine monolayer cells were infected with tachyzoites. Routinely, the established BPA1 and BPA2 cultures were passaged by adding a 1:8 dilution of needle-passaged monolayer in fresh media to cultures of uninfected bovine monolayers. By comparison, in our laboratory, cultures of *T. gondii* (RH isolate) are routinely passaged at a 1:200 dilution and *N. caninum* (NC-1 isolate) cultures are passaged at a 1:10 dilution every 2–3 days. As of mid-May 1992, cultures of the BPA1 and BPA2 isolates had been maintained with continuous growth for 10 and 6 months, respectively.

The results of an antigenic comparison of in vitro cultivated tachyzoites of BPA1 and BPA2 to those of cultivated *N. caninum* and *T. gondii* tachyzoites are shown in Table 2. The reactions of the bovine fetal isolates to the different antisera were similar to that demonstrated by *N. caninum*, and distinctly different from the pattern of reactivity observed with *T. gondii* tachyzoites (Table 2).

TABLE 2

Reactivity of in vitro cultivated tachyzoites with rabbit polyclonal antisera against different parasites in an immunoperoxidase test

| Parasite antigen | Antisera | | | | | |
|---|---|---|---|---|---|---|
| | Neospora caninum | Hammondia hammondi | \multicolumn{4}{c}{Toxoplasma gondii} |
| | | | Tg1 | Tg2 | Tg3 | Tg4 |
| Foetus 66 (BPA1) | +++ | – | – | + | – | – |
| Foetus 93 (BPA2) | +++ | – | ± | + | – | – |
| Neospora caninum | +++ | – | – | + | – | – |
| Toxoplasma gondii | – | +++ | +++ | +++ | +++ | +++ |

By transmission electron microscopy, the in vitro tachyzoites of isolates BPA1 and BPA2 were morphologically similar. Therefore, the following ultrastructural description applies to both isolates. Individual tachyzoites or clusters of multiple tachyzoites were usually located within a parasitophorous vacuole in the cytoplasm of bovine monolayer cells. Tachyzoites had a pellicle consisting of a complex of 2 inner membranes beneath a plasmalemmal membrane, a prominent nucleus in the central or posterior portion of the tachyzoite, 1 to 3 profiles of long tubular cristate mitochondria, a Golgi complex, rough and smooth endoplasmic reticulum, single- or multiple-membraned vesicles, and numerous free ribosomes. Ultrastructural apical features characteristic of apicomplexan parasites were present in tachyzoites of both isolates, including a polar ring which gave rise to 22 longitudinal subpellicular microtubules, a cylindrical or cone-shaped conoid within the polar ring and numerous electron dense rhoptries. The number of rhoptries visible in individual tachyzoites varied greatly and was dependent to some extent on the plane of section. A maximum of 24 rhoptries was counted in the anterior end of transversely sectioned tachyzoites. Rhoptries were not seen posterior to tachyzoite nuclei. In longitudinal sections, rhoptries were elongated, club-shaped structures with narrow, dense necks that extended into the conoid. As many as 14–32 electron-dense bodies were observed primarily posterior to the nucleus. Smaller numbers of these dense bodies were found anterior to the nucleus. Unlike rhoptries, dense bodies were generally round or oval in longitudinal sections. Large numbers of micronemes were seen in the anterior end of tachyzoites and only rarely observed posterior to the nucleus. The micronemes were most often arranged in organized arrays or sheets that were orientated parallel to the pellicular membrane or longitudinal axis of the tachyzoite. The number varied greatly in individual tachyzoites but as many as 60–100 micronemes were counted in longitudinal or oblique sections of selected tachyzoites. In addition, a single micropore, located anterior to the nucleus was seen in some tachyzoites. Parasites multiplied by endodyogeny and many were observed in the process of forming 2 progeny zoites within a single tachyzoite. Rarely, as many as 4 zoites with intact nuclei were seen in division but still attached to each other at the posterior end.

A concerted effort has been focused on the in vitro isolation of Neospora-like protozoal parasites from cattle after studies showed that they were the major diagnosed cause of abortion in California dairy cattle. Histologically, the two bovine fetuses from which isolates were first obtained in 1991 had compatible lesions, including multifocal non-supportive encephalitis, and protozoal tissue cysts like those seen in other natural infections of Neospora-like protozoa in bovine fetuses. The immunological reactivity of tissue cysts in the brains of fetus 66 and fetus 93 was also similar to that seen with many of the cysts in naturally infected fetuses which had strong reactions with *N. caninum* and *H. hommondi* antisera and occasional reactions to some of the *T. gondii* antisera.

Isolation of these Neospora-like protozoal parasites from aborted bovine fetuses was difficult because fetuses are generally moderately to severely autolyzed at the time of abortion and protozoal tissue cysts are present in a relatively small proportion of the infected fetuses. Previous ultrastructural studies suggested that most of the protozoal cysts in these fetal tissues were affected by autolysis and were probably non-viable (Barr et al. 1991 *Vet. Path.*28:110–16). The two fetuses from which isolates were obtained were in comparatively good postmortem condition. This fact, plus the relatively large number of cysts in these fetuses may have been critical factors in the successful isolation of the protozoal parasites. In addition, the isolation methods were modified. In particular, a longer period of trypsinization in preparing the brain material for cultivation, the overnight incubation of the brain homogenate on the monolayer, and use of the 87-3 bovine trophoblastic cell line for the initial parasite isolation were modifications in these procedures which appeared to be particularly helpful in obtaining the BPA1 and BPA2 isolates. Parasite growth was best maintained in 87-3 and CPAE monolayer cells. This contrasts with *N. caninum* and *Hammondia heydorni* which are reported to grow better in bovine monocyte cells (Speer et al. 1988 *Infect. and Immun.* 50:566–71).

In comparing these bovine protozoal isolates to those of *T. gondii* and *N. caninum* that have been re-isolated from mouse brains, it was found that the bovine protozoal isolates grew more slowly during isolation and after establishment of continuous growth. Whether this reflects a difference in the virulence of the organisms or a difference in adaptation to culture remains to be determined.

By light microscopy, tachyzoites of the bovine isolates were morphologically similar to in vitro tachyzoites of *T. gondii* and *N. caninum*. Cultivated tachyzoites of the bovine isolates had similar immunohistochemical reactions to tachyzoites of *N. caninum*, reacting strongly with *N. caninum* anti-serum and weakly to serum Tg1 which was produced by immunization of a rabbit with tachyzoite lysates of *T. gondii*. These antigenic reactions were distinctly different from those seen with culture-derived tachyzoites of *T. gondii*. Differences in antigenic reactivity of the cultivated BPA1 and BPA2 tachyzoites, as compared to those of tissue cysts in the source fetuses, could be explained by the stage-specific antigen expression of the different parasites and variations in the methods used to produce the antisera (i.e. immunization with cysts, oocysts or tachyzoite lysates). For example, tissue cyst wall antigens that reacted with antiserum to *H. hammondi* appeared to be lacking on tachyzoites of the bovine isolates in vitro. Unfortunately, a direct comparison of different parasite stages was not always possible since tachyzoites were not identified in the brains of the two bovine fetuses and true cysts have not been observed in the BPA1 or BPA2 cultures. Similarly, *N. caninum* tissue cysts and culture-derived *H. hommondi* tachyzoites were not available for comparison. Differences in antigenic expression may also be affected by host-specific factors. To evaluate this possibility, efforts are under way to obtain material from cattle, dogs, rats, cats and mice that have been experimentally infected with *N. caninum* or the bovine isolates so as to make a direct comparison of antigenic reactivity of the parasites in the same host species.

Thus far, characterization of the in vitro isolates from the two aborted bovine fetuses has shown that these parasites are antigenically and/or ultrastructurally distinct from *T. gondii, H. hommondi, S. cruzi*, Besnoitia spp. and Frenkelia spp. These isolates most closely resemble *N. caninum* parasites which have been most extensively studied in the U.S.A. and Scandinavia. The similarity between these parasites indicates that the BPA1 and BPA2 isolates belong to the genus Neospora. At present little is known about the lifecycle, including the definitive host, of these Neospora parasites in dogs or cattle. A better understanding of the biology of these parasites is essential to determine their taxonomic relationship to each other and to other apicomplexan parasites.

Example 2

This example describes an indirect fluorescent antibody (IFA) test for the detection of parasite-specific antibody responses in cattle that were naturally or experimentally infected with Neospora parasites. The methods used here are generally as described in Conrad et al. 1993 *J. Vet. Diagn. Invest.* 5:572–578 (1993).

MATERIALS AND METHODS
Parasites and antigen slide preparation

Antigen slides were prepared using tachyzoites of the BPA1 described above. Culture media consisted of Dulbecco's Minimum Essential Medium (DMEM) supplemented with 10% (v/v) heat-inactivated adult equine serum, 2 mM L-glutamine, 50 U/ml penicillin and 50 ug/ml streptomycin (DMEM-HS). Tachyzoites of *Toxoplasma gondii* (RH isolate; kindly provided by Dr. J. Boothroyd) were obtained from CPAE monolayer cultures grown in the same medium except that 10% (v/v) heat-inactivated fetal bovine serum was used instead of equine serum. Parasite-infected cultures were maintained in 25 or 75 $cm^2$ flasks incubated at 37° C. in an atmosphere of 5% $CO_2$.

Parasites were harvested for antigen preparation when ≧80% of the CPAE cells in the culture flask were infected with clusters of tachyzoites. The infected monolayer was removed from the flask by scraping into the medium and then passed 3× through a 25 ga needle to disrupt the cells. The suspension was passed through a 5 μm filter to remove cellular debris and tachyzoites were pelleted by centrifugation at 1300×g for 10 min. After removing the supernatant, the pellet was washed twice in sterile phosphate buffered saline pH 7.2 (PBS) and then resuspended in a modified PBS saline (137 mM NaCl, 3 mM KCl, 3 mM $Na_3C_6H_5O_7.2H_2O$, 0.4 mM $NaH_2PO_4.H_2O$, 12 mM $NaHCO_3$, 6 mM glucose) to a final concentration of approximately 2,000/μl. Aliquots of 10 μl of tachyzoite suspension were dispensed into each 4 mm well on 12-well heavy teflon coated (HTC) antigen slides. Slides were air-dried at room temperature and stored at −70° C.

Cattle

Test sera was obtained from naturally infected cows that aborted Neospora-infected fetuses, as well as congenitally infected calves. In addition, sera was obtained from two pregnant heifers that were experimentally infected at approximately 120 days gestation with tachyzoites of the BPA1 isolate derived from CPAE cultures. Tachyzoites were obtained from cultures using the procedure described for harvesting tachyzoites for antigen preparation except that the parasites were not washed in PBS and only the inoculum given to each heifer intravenously was filtered to remove cellular debris. After centrifugation, tachyzoites were resuspended in DMEM and administered by inoculation to each heifer so that $3 \times 10^6$ tachyzoites were given IV and $5 \times 10^6$ were given IM. A control heifer from the same herd and at the same stage of gestation was inoculated with an equivalent amount of uninfected CPAE cell culture material which was prepared and administered using the same procedures as for the infected heifers. Natural or experimental infections were confirmed by identification of Neospora tachyzoites and/or tissue cysts in fetal or calf tissues using an immunoperoxidase test procedure (Anderson et al. (1991) *J Am Vet Med Assoc* 198:241–244 and Barr et al. (1991) *Vet Path* 28:110–116).

For serological comparison with samples from Neospora-infected cattle, sera were obtained from the following additional sources: 1) cows that aborted fetuses which did not have lesions or parasites typical of Neospora infections, 2) weak calves that were suspected of having Neospora infections, but showed no lesions or parasites on postmortem histopathologic examination, 3) 20 heifers that were purchased as warnings from a closed beef herd in Todd County, Neb. and maintained under strict isolation, on range conditions at the Agricultural Research Development Center, University of Nebraska-Lincoln in Mead, Neb., 4) 20 pregnant heifers that were maintained on pasture in California and 5) 21 adult beef bulls or cows that were originally on pasture and then maintained in the same feedlot as the experimentally infected heifers.

Serum collection and testing

Test and control sera were obtained from blood samples that were collected by venipuncture into vacutainer tubes without anticoagulant. After storage at 4° C. for 2-12 hr, the blood was centrifuged at 500×g for 10 min and the serum was removed. Sera was stored either at 4° C. for <48 hr or frozen at −70° C. until tested.

Antigen slides were thawed at room temperature immediately prior to use. Sera were initially titrated in 2-fold dilutions from 1:40 to 1:40,960 to determine the end-point titer. Ten ul of diluted test or control sera were placed in separate wells on the antigen slides. Slides were incubated at 37° C. for 1 hr in a moist chamber, washed 3× for 5 min each in PBS, and then tapped gently to remove excess PBS. Fluorescein-labelled affinity-purified rabbit anti-bovine IgG diluted 1:500 in PBS was added in 10 ul aliquots to each well. Slides were incubated at 37° C. for 30 min, washed 3 times with PBS for 5 min each wash, tapped to remove excess PBS, cover-slipped with buffered glycerol (25% [w/v] glycerine in TRIS-HCL:pH 9.0), and examined at 200 magnification using a fluorescence microscope. The end-point titer was the last serum dilutions showing distinct, whole parasite fluorescence.

RESULTS

Natural infections

Sera collected at the time of abortion from 64 cows were tested for serologic reactivity to Neospora antigen (isolate BPA-1) using the IFA test procedure. Aborted fetuses from 55 of these cows had nonsuppurative encephalitis and/or myocarditis which was consistent with a protozoal infection. In addition tachyzoite and/or cyst stages of Neospora were identified by immunohistochemistry in the tissues of these 55 fetuses (Table 3). In the remaining 9 fetuses there was no indication of encephalitis and/or myocarditis and no detectable protozoal parasites. All of the cows that aborted Neospora-infected fetuses had titers of 320 to 5,120 to Neospora antigens (Table 3). Eight of the cows that aborted fetuses with no detectable Neospora parasites had titers ≦160 and one had a titer of 320.

TABLE 3

Titers of cow sera collected after abortion of Neospora-infected fetuses to bovine Neospora (BPA1 isolate) antigens.

| Neospora titer | Number of cows | Neospora tissue stages in fetus | | |
|---|---|---|---|---|
| | | cysts | tachys | cysts & tachys |
| 320 | 1 | 0 | 1 | 0 |
| 640 | 12 | 2 | 8 | 2 |
| 1280 | 12 | 2 | 10 | 0 |
| 2560 | 15 | 2 | 11 | 2 |
| 5120 | 15 | 5 | 7 | 3 |

Figure 2:
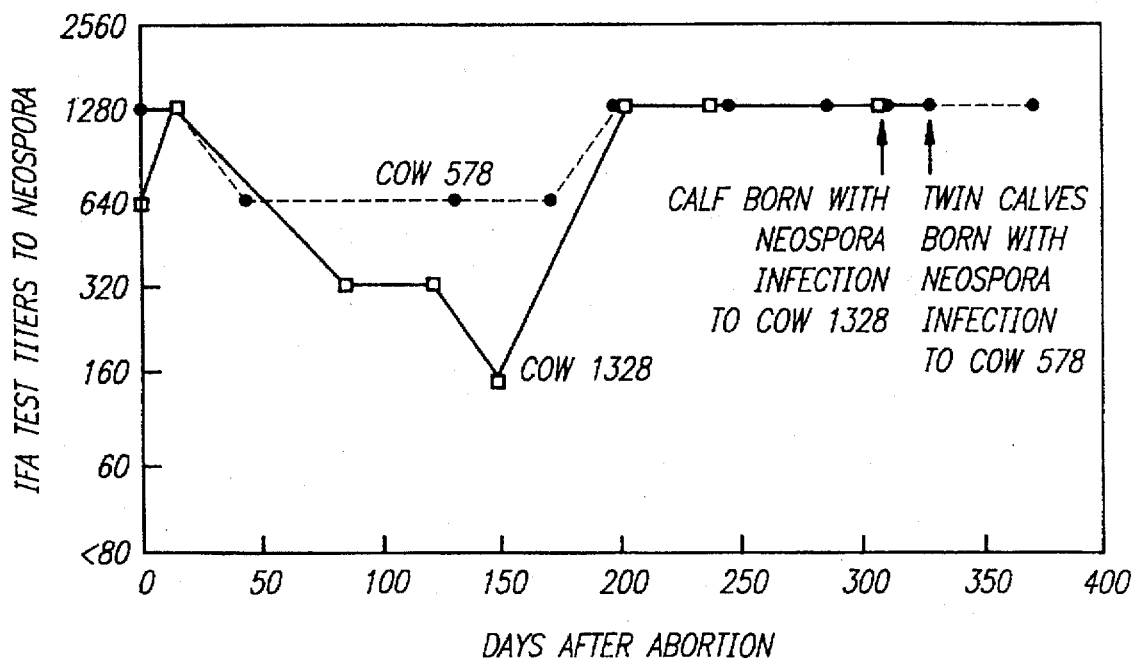
FIG. 2 shows IFA test titers of serial samples from two cows that aborted Neospora-infected fetuses and subsequently delivered congenitally infected calves.

Six of the cows that aborted Neospora-infected fetuses were maintained on their 4 dairies of origin so that these cows could be tested repeatedly over a 6 to 12 month period to determine changes in the Neospora titer. Peak titers of 640 to 2,560 were apparent within the first 20 days after abortion in all of the cows (FIGS. 1 & 2). Subsequently, the titers of 4 of the cows (FIG. 1, cows 9, 970 & 522; FIG. 2, cow 578) decreased to 640, whereas the titers of cow 3 (FIG. 1) and cow 1328 (FIG. 2) dropped to 160 within 150 days post-abortion. Cows 578 and 1328 were rebred and became pregnant again within approximately 50 to 70 days of aborting Neospora-infected fetuses. When these cows were approximately 4 to 5 months pregnant their Neospora titers increased to their original peak levels of 1,280 and remained at this level until the cows gave birth to full-term calves (FIG. 2). The calf born to cow 1328 had a pre-colostral titer of 20,480 and twin calves born to cow 578 both had precolostral titers of 10,240 to the bovine Neospora isolate. Upon necropsy at 2 to 6 days of age, these calves showed mild nonsuppurative encephalomyelitis or focal mononuclear cell infiltrates the brain parenchyma. Neospora tissue cysts were seen in association with inflammatory lesions in all 3 calves. The post-colostral titers of sera taken from each calf prior to euthanasia were the same as their precolostral titers.

Serologic titers were determined for four additional calves that were diagnosed as having congenital Neospora infections based on the presence of characteristic cyst stages in the brain and/or spinal cord which reacted immunohistochemically with antisera to the BPA-1 bovine Neospora isolate. Neospora was isolated from the brains and/or spinal cords of calves 1-3 and the parasites were grown continuously in vitro, using a previously described method for isolation of Neospora from aborted bovine fetuses. At necropsy, calves 1 and 2 had Neospora titers of 20,480, calf 3 had a titer of 10,240 and calf 4 had a titer of 5,120. Sera collected from the dam of calf 4 at calving had a Neospora titer of 2,560. Precolostral calf sera and sera from the dams of calves 1-3 were not available for testing.

The titers observed in the 7 congenitally infected calves with confirmed Neospora infections were markedly greater than those obtained with sera from 4 weak 1-5 day old calves which were suspected of having Neospora infections, but showed no histopathologic evidence of characteristic lesions or parasites on post-mortem examination. One of these uninfected calves had a titer of 160, while the others had titers <80 to bovine Neospora antigens. Whether or not these calves had received colostrum was not known.

Experimental infections

Figure 3:
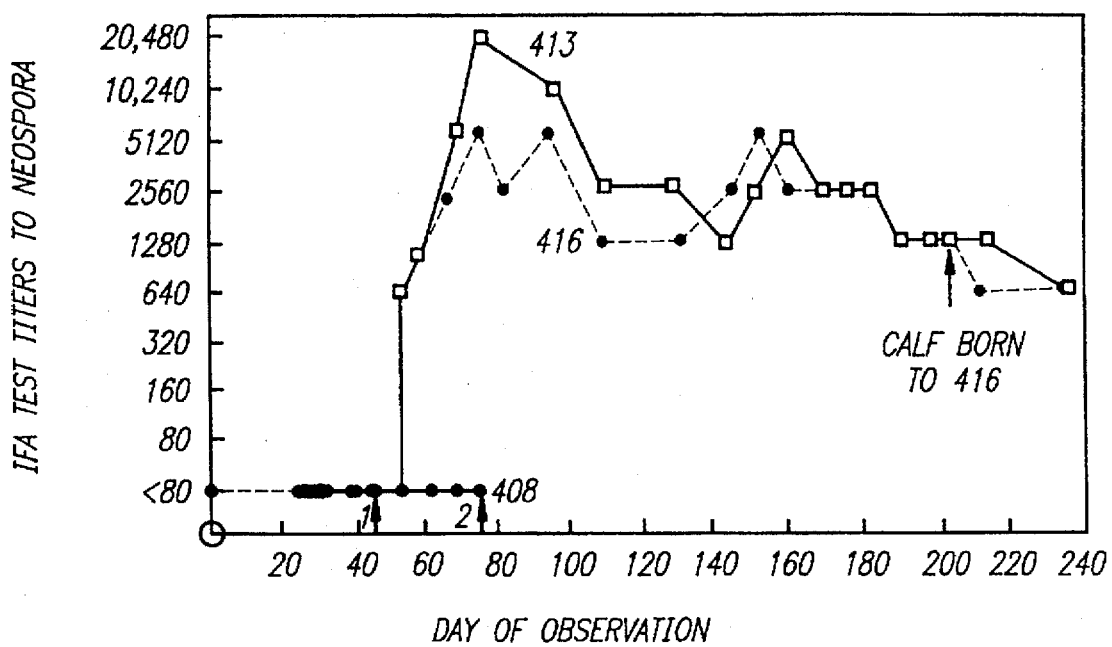
FIG. 3 shows seroconversion by heifers experimentally infected with Neospora.

Repeated sera samples taken from the 3 pregnant heifers prior to experimental inoculation on day 43 had titers of <80 to Neospora BPA1 antigens. The 2 heifers that were infected with culture-derived tachyzoites of the BPA1 bovine isolate developed Neospora titers of 640 by day 9 and 1,280 by day 18 after parasite inoculation (FIG. 3). The heifer that received uninfected cell culture material had titers <80 to Neospora antigens throughout the experiment. She was euthanitized 32 days after inoculation to remove her fetus which was viable, histologically normal and uninfected, with no detectable titer to Neospora. Peak titers for both infected heifers were detected 32 days after parasite inoculation, at which time the fetus of heifer 413 was removed by caesarian section. Histologically, the fetus had inflammatory lesions and numerous Neospora tachyzoites present in its central nervous system. In addition, Neospora tachyzoites were isolated from fetal tissues and grown continuously in cell culture. Sera collected from the fetus had a titer of 640 to Neospora antigens. After her fetus was removed, the Neospora titer of heifer 413 fluctuated between 1,280 and 5,120, until day 193 post-infection when it dropped to 640 (FIG. 3). Heifer 416 calved 158 days after parasite inoculation at which time she had a Neospora titer of 1,280 (FIG. 3). The calf had a precolostral Neospora titer of 10,240 which was the same as the sample which was collected 2 days later, after ingestion of the dam's colostrum. Clinically the calf appeared normal except that it had decreased conscious proprioception in all 4 limbs when examined prior to euthanasia at 2 days of age. There were minimal histological lesions, consisting of focal gliosis in the central nervous system, but no parasites were detected in fetal tissues.

Uninfected cattle

Fifty three of the 61 (87%) adult cattle tested which had no history of Neospora infection had titers ≦80, and all but one animal had titers ≦160 to both Neospora and Toxoplasma antigens (Table 4). The pastured cattle that were moved and subsequently maintained under feedlot conditions did not have higher serologic titers to tachyzoites of bovine Neospora or *Toxoplasma gondii* than those kept on pasture. End-point titer determinations of all samples from infected or uninfected cattle were always based on whole tachyzoite fluorescence. However, in testing the apparently uninfected animals, sera samples from 3 of the cows and 7 of the bulls that were housed in the UCD feedlot had parasite fluorescence which was restricted to the apical end of the parasite. This reaction was particularly marked with the 7 sera from bulls which had apical fluorescence titers of 160 to 320 to both Neospora and Toxoplasma, while the whole parasite fluorescence titer was ≦80.

TABLE 4

Titers of sera from cattle with no evidence of Neospora infection to bovine Neospora (BPA1 isolate) and *Toxoplasma gondii*.

| Cattle | Location | Neo titer | Number positive | Toxo titer | Number postive |
|---|---|---|---|---|---|
| 20 heifers | Nebraska pasture | ≦80 | 16 | ≦80 | 14 |
| | | 160 | 3 | 160 | 6 |
| | | 320 | 1 | | |
| 20 heifers | California pasture | ≦80 | 17 | ≦80 | 13 |
| | | 160 | 3 | 160 | 3 |
| | | | | ND | 4 |
| 9 cows | UCD feedlot | <80 | 9 | ≦80 | 7 |
| | | | | 160 | 2 |
| 12 bulls | UCD feedlot | ≦80 | 11 | ≦80 | 10 |
| | | 160 | 1 | 160 | 2 |

Figure 4:
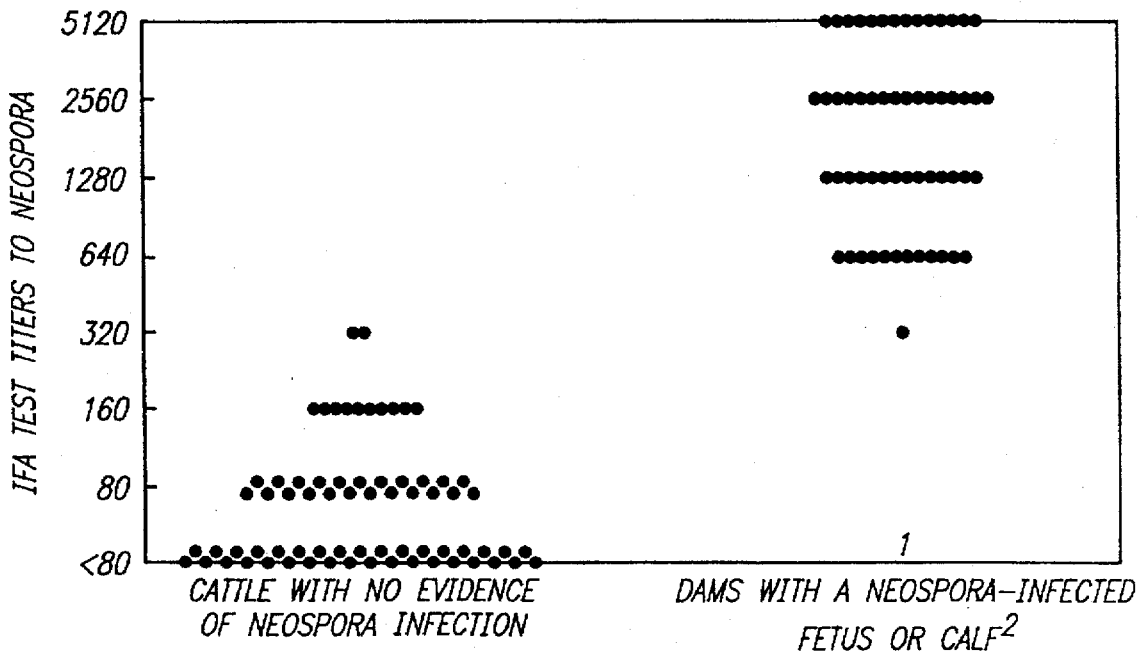
FIG. 4 shows IFA test titers: comparing cattle with no evidence of infection to dams with Neospora-infected fetuses or calves.

FIG. 4 shows the serologic titers of the 61 uninfected adult cattle plus the 9 cows that aborted fetuses without evidence of Neospora infections compared to the titers of Neospora-infected cows at the time of abortion or calving. Although a majority of the infected cattle had titers ≧1280 to Neospora and most of the cattle that had no evidence of infection had titers ≦80, there was some overlap between these groups in the 160 to 640 titer range (FIG. 4).

Example 3

This example describes isolation of DNA encoding nss-rRNA (sequence shown in FIG. 5).

Parasites

Bovine Neospora isolates BPA-1 BPA-2, BPA-3, BPA-4, BPA-5 were used for DNA isolation. Parasites were harvested for DNA preparation when >80% of the CPAE cells were infected with large clusters of tachyzoites. The infected monolayer was removed from the flask by scrapping. The tachyzoites in tissue culture media were pelleted by centrifugation at room temperature, 1300×g for 10 minutes. The supernatant was removed and the pellet was resuspended in 10 mls sterile physiologically buffered saline (PBS: pH 7.4), passed through a 25 gauge needle three times to disrupt the CPAE cells, and then filtered through a 5 um disc filter (Gelman Sciences, Acrodisc) to remove cellular debris. The filtered material was pelleted at 1300×g for 10 minutes and washed in PBS (pH 7.4). The supernatant was removed and the tachyzoite pellet was stored at −70° C. until used. Uninfected CPAE monolayer cells were processed by the same procedure and used as controls.

Two methods were used to prepare the DNA from the tachyzoites and control CPAE cells. Initially, DNA was prepared as follows. Briefly, the parasite or control cell pellets were suspended in 1.0 ml STE with 0.5% SDS treated with proteinase K (100 µg/ml) and RNAase (100 µg/ml) then extracted twice with phenol, once with phenol-chloroform-isoamyl alcohol, and once with chloroform-isoamyl alcohol. DNA was subsequently precipitated with ethanol, dried and resuspended in TE buffer. Other DNA samples were prepared with the Isoquick DNA Extraction kit (Microprobe, Corp., Garden Grove, Calif.) following manufacturer's directions.

DNA preparations were electrophoresed in 0.8% (w/v) agarose (FMC) Bioproducts) in 0.5M Tris/borate/EDTA (TBE) buffer (89 mM Tris, 89 mM boric acid, 2 mM EDTA) gels stained with ethidium-bromide (0.5 ug/ml) and examined under by ultraviolet (UV) light.

Amplification of rRNA gene sequences:

DNA sequences were amplified by the polymerase chain reaction (PCR) using a programmable thermal cycler (Perkin-Elmer). Reactions were performed in 50 to 100 ul volume samples containing approximately 50–100 ng of DNA template, 50 mM Tris buffer (pH 8.3), 1.0 mM $MgCl_2$, 200 mM of each of the four deoxynucleoside triphosphates, 0.5 U of Taq polymerase (Promega) and 100 pM of universal primer A (5'CCG AAT TCG TCG ACA CCT GGT TGA TCC CCG ACG ACC GTG GTC TGA ACG GGA G' (SEQ ID NO.:2)) and primer C (5'GGG CCC TAG GTG GCG CCG ACG ACC GTG GTC TGA ACG GGA G 3' (SEQ ID NO.:3)). The PCR cycling parameters consisted of a single step at 94° C. for 3 minutes followed by 30 cycles denaturation at 94° C. for 1 minute, 1 minute of annealing at 55, and 2 minutes of extension at 72 with a final extension step of 7 minutes. The PCR amplification product was an approximately 550-bp sequence from the 5' end of the nss-rRNA gene. A more extensive 1.8 kb sequence of the nss-rRNA gene was amplified from BPA1 DNA using universal primer A and primer B (5'CCC GGG ATC CAA GCT TGA TCC TTC TGC AGG TTC ACC TAC 3' (SEQ ID NO.:4)).

These reactions were performed using 50 ul reaction samples that contained 100 pM of each primer, 1 mM $MgCl_2$, 50–100 ng of template DNA, 50 mM Tris buffer (pH 8.3), 1.0 mM $MgCl_2$, a 200 mM of each of the four deoxynucleoside triphosphates (dATP, dCTP, dGTP, and dTTP), and 0.5 U of Taq polymerase (Promega). The amplification cycles were performed by an initial denaturation step at 94° C. for 3 minutes followed by 45 cycles of denaturation at 94° C. for 1 minute, 1 minute of annealing at 55° C., and 4 minutes of extension at 72° C. with the final extension step for 7 minutes. For both amplification reactions, the stationary CPAE cell DNA was used as the negative template control. Sterile water was used for the PCR reaction condition controls. Aliquots of each PCR product were sized by comparison with DNA standards (Bioventures, Inc. TN) after electrophoresis through a 3% (w/v) NuSieve, 1% (w/v) SeaKem agarose gel (FMC BioProducts, Rockland Me.) stained with ethidium bromide and visualized under UV light.

Amplification products from 3 to 5 reactions were pooled prior to purification to reduce the possibility of any nucleotide misincorporation errors by the Taq polymerase during the elongation step of the newly synthesized complement strain. The PCR amplification products were purified either by gel electroelution or by spin-columns. Two different spin-columns were used at different times. First, Magic PCR Prep DNA purification System (Promega Corp.) was used following manufacturer's directions. Briefly, the products were electrophoresed through a low temperature melting agarose (Low Melt Agarose, FMC BioPorducts,). The DNA was visualized in the gel by ethidium bromide staining and the DNA band was excised into an eppendorf tube. The agarose and DNA were heated (70° C.) to melt the agarose. The DNA was separated from the agarose using columns and reagents provided in the kit. Later simpler and less time intensive methods were used by purifying the PCR products using the PCR Select II (5 Primer-3 Prime, Inc) columns which do not require electrophoresis and excision of the product in low melt agarose.

DNA sequencing of the purified PCR products were performed following manufacturer's instructions for the PCR Cycle Sequencing System (BRL ds DNA Cycle Sequencing System). The cycling parameters consisted of a two step program after complete denaturation at 95° C. for 3 minutes. The first program step amplified DNA using 20 cycles that included 30 seconds for denaturation, 30 seconds for annealing, and 1 minute of extension. The second program step alternated between denaturation (95° C.) and extension (72° C.) only. Initially, the universal primers (A, C or B) were used to obtain the first nucleotide sequence data from which internal primers could be constructed and used to amplify internal sequences. All sequencing primers were 5' labelled with adenosine 5'[$\gamma^{32}$P] triphosphate (Amersham). Reactions were heated to 95° C. for 5 minutes prior to loading onto either a 6% (w/v) or 8% (w/v) polyacrylamide, 8M urea (0.4 mm thick) non-gradient gel using a Model S2 Sequencing Gel Apparatus (GIBCO BRL, Gaithersburg, Md.). The sequencing gels were fixed in 10% acetic acid and 10% methanol to remove the urea prior to transfer of the sequencing products in the gel onto filter paper. The gels were dried using a gel drying apparatus (Biorad Gel Drier, X) for 1 to 2 hours at 70°–80° C. The membrane filters were autoradiographed using Kodak X-OMAT X-ray film.

DNA Sequence analysis:

DNA sequences were constructed from at least 3 separate reactions to ensure the accuracy of the nucleotide sequence data obtained. Autoradiographs of the sequencing products were read using Hibio MacDNASIS DNA and Protein Sequence Analysis System (Hitachi Software Engineering Co,). This program and the GCG programs (SEQED, Fragment Assembly, Lineup, and Pretty) (University of Wisconsin Genetics Computer Group) on a VMS system facilitated the construction of the DNA sequences.

Example 4

The DNA prepared in Example 3 was used to design primers and probes for the detection of Neospora. The protocol used was as follows.

Oligonucleotide PCR primers:

1) Bovine Neospora Forward Primer (5'-AAGTATAAGCTTTTATACGGCT-3' (SEQ ID NO.:5))

2) Bovine Neospora Reverse Primer (5'-CACTGCCACGGTAGTCCAATAC-3' (SEQ ID NO.:6))

DNA amplification was carried out in a total volume of 50 µl. The reaction mixture contained 10 mM Tris-HCl (pH 9.0), 50 mM potassium chloride, 0.1% Triton X-100, 1.0 mM magnesium chloride, 200 mM of each deoxynucleoside triphosphates, 0.42 µM Bovine Neospora Forward primer and 0.384 µM Bovine Neospora Reverse primer. After precycle denaturation at 94° C. for 4 min to reduce nonspecific amplification, 2.5 U of Taq DNA polymerase (Promega Corp., Madison, Wis.) was added and the mixture was overlaid with 50 µl of mineral oil. Amplification was performed in a DNA Thermal Cycler (Perkin Elmer Cetus Corp., Norwalk, Conn.) for 31 cycles as follows: denaturation at 94° C. for 1 min, annealing at 54° C. for 1 min, and extension at 72° C. for 2 min. The last cycle was given a prolonged extension period of 7 min. After amplification, 5 µl of each sample or a BioMarker Low (BioVentures, Inc., Murfreeboro, Tenn.) DNA size standard were mixed with 1 µl of 6× loading dye and electrophoresed on a 3% Nusieve 3:1 agarose gel (FMC Bioproducts). The gel was stained in a 0.5 µg/ml ethidium bromide solution for 30 min and observed for the presence of amplification products under ultraviolet illumination.

Oligonucleotide DNA probes:

3) BPA/Neospora Internal Probe Sequence (5'-AGTCAAACGCG-3' (SEQ ID NO.:7))

4) Toxoplasma Internal Probe Sequence (5'-AAGTCAACGCG-3' (SEQ ID NO.:8))

Amplification products were denatured in the gel and transferred to nylon membranes (Hybond-N; Amersham Corp., Arlington Heights, Ill.) by Southern blotting method. DNA was cross-linked to nylon membrane using a Stratalinker UV crosslinker (Stratagene, La Jolla, Calif.). Prehybridization, preparation of the labeled internal probe, and hybridization were performed as recommended by the manufacturer for the Enhanced Chemiluminescence 3'-oligolabeling and Detection Systems (Amersham). Labeled internal probe was added to a final concentration of 10 ng/ml of hybridization solution and incubated overnight at 30° C. with gentle agitation. After hybridization, the membranes were washed twice for 5 min each at room temperature in 5× SSC and 0.1% (w/v) SDS, and then washed twice for 5 min each at room temperature in 0.5× SSC and 0.1% (w/v) SDS. Membrane blocking, antibody incubations, signal generation and detection were performed as described by the manufacturer. Membranes were exposed to Kodak X-Omat film for 3–10 min.

Results

Using the Neospora-specific primers 294 bp PCR products were amplified from DNAs of BPA-1 and Toxoplasma (RH and BT isolates). In addition, a 350 bp product was amplified from *Sarcocystis cruzi* DNA. No products were produced with DNAs from various bacteria, CPAE cells, and bovine thymocytes. Only the Neospora-specific probe hybridized to the Neospora amplification product. Similarly, the Toxoplasma-specific hybridized only to the Toxoplasma amplification product.

Example 5

This example describes experimental infections of pregnant cows with culture-derived Neospora tachyzoites.

Three cows were inoculated with $8\times10^6$ tachyzoites of the BPA1 Neospora isolate ($3\times10^6$ tachyzoites IV, and $5\times10^6$ tachyzoites IM). These cows were inoculated at 95 days gestation (Cow #412), 100 days gestation (Cow #416), and 105 days gestation (Cow #413). In each case, a Neospora fetal infection was confirmed (Cow #412 expelled an infected mummified fetus; Cow #416 gave birth to a calf that was in utero exposed; and an infected fetus was removed surgically from Cow #416). Two control cows were inoculated with uninfected cell culture and gave birth to uninfected live calves.

These cows were kept and rebred without any intervention. All three experimental cows gave birth to seronegative, clinically normal calves (not all post mortem tissues examined to date).

The cows were kept and rebred once again. The previously infected cows (#s 412, 416, 413 were then rechallenged by giving them the same inoculum ($8\times10^6$ tachyzoites, divided and given IV and IM) at 89, 83, and 83 days gestation, respectively. Control cows were rebred and observed. Two infected cows (#s 413 and 416) gave birth to live calves which were clinically normal and seronegative to Neospora antigens. The third cow (#412) aborted 27 days post inoculation. The fetus was recovered. Although mild lesions suggestive of Neospora infection were found, Neospora infection, to date, has not been confirmed (formalin-fixed paraffin embedded tissues negative by immunohistochemistry). The cow was rebred and resorbed its fetus. She was rebred again and she aborted once again at 97 days gestation. This second fetus was not recovered. Thus far histopathologic examination or the tissues from the two clinically normal calves indicates that they were not tranplacentally infected with Neospora parasites.

This is the first experiment to show that cattle can be protected against Neospora abortion by immunization with culture-derived tachyzoites of the BPA-1 Neospora isolate.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A biologically pure culture of bovine Neospora having all the ultrastructural and antigenic characteristics of a Neospora isolate selected from the group consisting of BPA1 having ATCC Accession No. 75710 and BPA6 having ATCC Accession No. 75711.

2. The culture of claim 1, which is selected from the group consisting of BPA1 having ATCC Accession No. 75710 and BPA6 having ATCC Accession No. 75711.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 1747 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
AGTCATATGC TTGTCTTAAA GATTAAGCCA TGCATGTCTA AGTATAAGCT TTTATACGGC      60
TAAACTGCGA ATGGCTCATT AAAACAGTTA TAGTTTATTT GATGGTCTTT ACTACATGGA     120
TAACCGTGGT AATTCTATGG CTAATACATG CGCACATGCC TCTTCCTCTG GAAGGGCAGT     180
GTTTATTAGA TACAGAACCA ACCCACCTTC CGGTGGTCCT CGGGTGATTC ATAGTAACCG     240
AACGGATCGC GTTTGACTTC GGTCTGCGAC GGATCATTCA AGTTTCTGAC CTATCAGCTT     300
TCGACGGTAC TGTATTGGAC TACCGTGGCA GTGACGGGTA ACGGGAATT  AGGGTTCGAT     360
TCCGGAGAGG GAGCCTGAGA AACGGCTACC ACATCTAAGG AAGGCAGCAG GCGCGCAAAT     420
TACCCAATCC TGATTCAGGG AGGTAGTGAC AAGAAATAAC AACACTGGAA ATTTCATTTC     480
TAGTGATTGG AATGATAGGA ATCCAAACCC CTTCAGAGT  AACAATTGGA GGGCAAGTCT     540
GGTGCCAGCA GCCGCGGTAA TTCCAGCTCC AATAGCGTAT ATTAAGTTG  TTGCAGTTAA     600
AAAGCTCGTA GTTGGATTTC TGCTGGAAGC AGCCAGTCCG CCCTCAGGGG TGTGCACTTG     660
GTGAATTCTA GCATCCTTCT GGATTTCTTC ACACTTCATT GTGTGGAGTT TTTTCCAGGA     720
CTTTTACTTT GAGAAAATTA GAGTGTTTCA AGCAGGCTTG TCGCCTTGAA TACTGCAGCA     780
TGGAATAATA AGATAGGATT TCGGCCCTAT TTTGTTGGTT TCTAGGACTG AAGTAATGAT     840
TAATAGGGAC GGTTGGGGGC ATTCGTATTT AACTGTCAGA GGTGAAATTC TTAGATTTGT     900
TAAAGACGAA CTACTGCGAA AGCATTTGCC AAAGATGTTT TCATTAATCA AGAACGAAAG     960
TTAGGGGCTC GAAGACGATC AGATACCGTC GTAGTCTTAA CCATAAACTA TGCCGACTAG    1020
AGATAGGAAA ACGTCATGCT TGACTTCTCC TGCACCTTAT GAGAAATCAA AGTCTTTGGG    1080
TTCTGGGGGG AGTATGGTCG CAAGGCTGAA ACTTAAAGGA ATTGACGGAA GGGCACCACC    1140
AGGCGTGGAG CCTGCGGCTT AATTTGACTC AACACGGGGA AACTCACCAG GTCCAGACAT    1200
AGGAAGGATT GACAGATTGA TAGCTCTTTC TTGATTCTAT GGGTGGTGGT GCATGGCCGT    1260
TCTTAGTTGG TGGAGTGATT TGTCTGGTTA ATTCCGTTAA CGAACGAGAC CTTAACCTGC    1320
```

| | | | | | |
|---|---|---|---|---|---|
|TAAATAGGAT|CAGGAACTTC|GTGTTCTTGT|ATCACTTCTT|AGAGGGACTT|TGCGTGTCTA|1380
|ACGCAAGGAA|GTTTGAGGCA|ATAACAGGTC|TGTGATGCCC|TTAGATGTTC|TGGGCTGCAC|1440
|GCGCGCTACA|CTGATGCATC|CAACGAGTTT|ATAACCTTGG|CCGATAGGTC|TAGGTAATCT|1500
|TGTGAGTATG|CATCGTGATG|GGGATAGATT|ATTGCAATTA|TTAATCTTCA|ACGAGGAATG|1560
|CCTAGTAGGC|GCAAGTCAGC|AGCTTGCGCC|GATTACGTCC|CTGCCCTTTG|TACACACCGC|1620
|CCGTCGCTCC|TACCGATTGA|GTGTTCCGGT|GAATTATTCG|GACCGTTTTG|TGGCGCGTTC|1680
|GTGCCCGAAA|TGGGAAGTTT|TGTGAACCTT|AACACTTAGA|GGAAGGAGAA|GTCGTAACAA|1740
|GGTTTCC| | | | |1747

( 2 ) INFORMATION FOR SEQ ID NO:2:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

CCGAATTCGT CGACACCTGG TTGATCCCCG ACGACCGTGG TCTGAACGGG AG    52

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GGGCCCTAGG TGGCGCCGAC GACCGTGGTC TGAACGGGAG    40

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

CCCGGGATCC AAGCTTGATC CTTCTGCAGG TTCACCTAC    39

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

AAGTATAAGC TTTTATACGG CT    22

( 2 ) INFORMATION FOR SEQ ID NO:6:

( i ) SEQUENCE CHARACTERISTICS:

-continued ( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:6:

CACTGCCACG GTAGTCCAAT AC 22

( 2 ) INFORMATION FOR SEQ ID NO:7:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:7:

AGTCAAACGC G 11

( 2 ) INFORMATION FOR SEQ ID NO:8:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:8:

AAGTCAACGC G 11